United States Patent
Zhang et al.

(10) Patent No.: US 11,891,573 B2
(45) Date of Patent: Feb. 6, 2024

(54) METHOD AND DEVICE FOR CONTROLLING VISCOSITY OF ASPHALT RUBBER BASED ON CURRENT VARIATION

(71) Applicants: GUANGXI TRANSPORTATION SCIENCE AND TECHNOLOGY GROUP CO., LTD., Guangxi (CN); GUANGXI JIAOKE NEW MATERIALS TECHNOLOGY CO.,LTD., Guangxi (CN)

(72) Inventors: Honggang Zhang, Guangxi (CN); Hongbo Zhang, Guangxi (CN); Haitao Yuan, Guangxi (CN); Jizong Tan, Guangxi (CN); Baolin Xiong, Guangxi (CN); Yong Wang, Guangxi (CN); Jianchun Yan, Guangxi (CN); Yehao Yin, Guangxi (CN); Xiaolei Wang, Guangxi (CN)

(73) Assignees: GUANGXI TRANSPORTATION SCIENCE AND TECHNOLOGY GROUP CO., LTD., Guangxi (CN); GUANGXI JIAOKE NEW MATERIALS TECHNOLOGY CO., LTD., Guangxi (CN)

( * ) Notice: Subject to any disclaimer, the term of this patent is extended or adjusted under 35 U.S.C. 154(b) by 128 days.

(21) Appl. No.: 17/680,780

(22) Filed: Feb. 25, 2022

(65) Prior Publication Data
US 2022/0267677 A1    Aug. 25, 2022

(30) Foreign Application Priority Data
Feb. 25, 2021    (CN) .......................... 202110210883.9

(51) Int. Cl.
*C10C 3/00* (2006.01)
*C08L 95/00* (2006.01)

(52) U.S. Cl.
CPC ................ *C10C 3/00* (2013.01); *C08L 95/00* (2013.01)

(58) Field of Classification Search
CPC .................................... C10C 3/00; C08L 95/00
See application file for complete search history.

(56) References Cited

U.S. PATENT DOCUMENTS

| | | | | |
|---|---|---|---|---|
| 3,965,722 A | * | 6/1976 | Bagg .................. | G01N 11/14 |
| | | | | 73/54.31 |
| 2005/0087002 A1 | * | 4/2005 | Kanzaki ............... | B01F 33/453 |
| | | | | 73/54.28 |

FOREIGN PATENT DOCUMENTS

WO    WO-2021027248 A1 *    2/2021    .............. C08J 11/10

* cited by examiner

*Primary Examiner* — Randy Boyer
(74) *Attorney, Agent, or Firm* — Millen, White, Zelano & Branigan P.C.; William F. Nixon

(57) ABSTRACT

A method and device for controlling viscosity of asphalt rubber based on a current variation are provided. The method includes processing asphalt rubber raw materials with a first preset proportion, and shearing the processed asphalt rubber; obtaining a shearing current, pumping and discharging the sheared asphalt rubber; obtaining a discharging current, and obtaining the viscosity of the pumped asphalt rubber according to the discharging current and the viscosity-discharging current correlation relationship. The method includes comparing the viscosity with a preset viscosity; outputting the pumped asphalt rubber as finished asphalt rubber when the viscosity is equal to the preset viscosity. The method includes adjusting the viscosity according to the discharging current. Double-current control is adopted, so that the whole-process control of the processing viscosity of the asphalt rubber is realized, and the control accuracy of the viscosity is improved.

6 Claims, 2 Drawing Sheets

METHOD AND DEVICE FOR CONTROLLING VISCOSITY OF ASPHALT RUBBER BASED ON CURRENT VARIATION

CROSS REFERENCE TO RELATED APPLICATION

This patent application claims the benefit and priority of Chinese Patent Application No. 202110210883.9 filed on Feb. 25, 2021, the disclosure of which is incorporated by reference herein in its entirety as part of the present application.

TECHNICAL FIELD

The present disclosure relates to the viscosity control field of asphalt rubber, in particular to a method and device for controlling the viscosity of the asphalt rubber based on a current variation.

BACKGROUND ART

With the great progress of automobile industry, waste tires which seriously pollute the environment are generated. According to the research, the methods of obtaining rubber powder by utilizing the waste tires, doping rubber powder into matrix asphalt and the like are effective ways for solving the pollution of the waste tires. The viscosity of the asphalt rubber is higher than that of the traditional modified asphalt, and an asphalt mixture and a paving and rolling mode are suitable within an appropriate viscosity range of the rubber, otherwise, the construction is difficult. However, the processing quality of the asphalt rubber is not stable enough, and particularly in a case of the field processing or an urgent production task, the processing quality of the asphalt rubber is difficult to detect, adjust and control in time, so that the indexes, such as the viscosity of the asphalt rubber, are not stable, and the production of a mixing station and the smooth paving and rolling in the front field are influenced. Therefore, a method and device capable of accurately controlling the viscosity of asphalt rubber are urgently needed.

SUMMARY

The purpose of the present disclosure is to provide a method and device for controlling viscosity of asphalt rubber based on a current variation, in which the viscosity of the asphalt rubber is timely and accurately adjusted and controlled by detecting the shearing current and the discharging current, so that the asphalt rubber meeting the preset viscosity requirement can be output, the accuracy of controlling the viscosity of the asphalt rubber is improved, and the stability of asphalt rubber production is ensured.

In order to achieve the purpose described above, the present disclosure provides the following solution:

A method for controlling viscosity of asphalt rubber based on a current variation comprises:
  processing asphalt rubber raw materials with a first preset proportion, and shearing the processed asphalt rubber;
  obtaining a shearing current, and determining whether the shearing of the processed asphalt rubber is completed according to the shearing current; and pumping and discharging the sheared asphalt rubber;
  obtaining a discharging current, and obtaining the viscosity of the pumped asphalt rubber according to the discharging current and the viscosity-discharging current correlation relationship;
  comparing the viscosity of the pumped asphalt rubber with a preset viscosity value, and outputting the pumped asphalt rubber as finished asphalt rubber when the viscosity of the pumped asphalt rubber is equal to the preset viscosity value; and
  adjusting the viscosity of the pumped asphalt rubber according to the discharging current when the viscosity of the pumped asphalt rubber is not equal to the preset viscosity value.

Optionally, before the processed asphalt rubber is sheared, the processing time is required to reach a preset processing time.

Optionally, obtaining the shearing current and determining whether the shearing of the processed asphalt rubber is completed according to the shearing current, specifically comprises:
  obtaining the shearing current in a preset shearing time period, and completing the shearing of the processed asphalt rubber when the shearing current is equal to a preset shearing current value;
  adding the currently sheared asphalt rubber into the asphalt rubber raw materials with a first proportion for processing again when the shearing current is lower than the preset shearing current value, and returning to the step of "shearing the processed asphalt rubber" until the shearing current is equal to the preset shearing current value, wherein the first proportion is determined according to the shearing current and the preset shearing current value; and
  prolonging the shearing time when the shearing time reaches the preset shearing time and the shearing current is higher than the preset shearing current value, until the shearing current is equal to the preset shearing current value.

Optionally, obtaining the viscosity-discharging current correlation relationship, comprises:
  processing asphalt rubber raw materials with a second preset proportion, shearing the processed asphalt rubber, and pumping and discharging the sheared asphalt rubber;
  obtaining the discharging current, and meanwhile detecting the viscosity of the pumped asphalt rubber;
  adjusting the value of the second preset proportion again, and returning to the step of "processing asphalt rubber raw materials with a second preset proportion" until multiple groups of the discharging current and viscosity of the pumped asphalt rubber are obtained; and
  carrying out curve fitting on the multiple groups of the discharging current and viscosity of the pumped asphalt rubber to obtain the viscosity-discharging current correlation relationship.

Optionally, an expression of the viscosity-discharging current correlation relationship is $y=0.26x-5.32$, wherein y represents the viscosity of the pumped asphalt rubber, and x represents the discharging current.

Optionally, adjusting the viscosity of the pumped asphalt rubber according to the discharging current when the viscosity of the pumped asphalt rubber is not equal to the preset viscosity value, specifically comprises:
  shearing the pumped asphalt rubber again when the discharging current is higher than a preset discharging current value, and returning to the step of "obtaining the shearing current" until the viscosity of the pumped asphalt rubber meets the preset viscosity value; and
  adding the pumped asphalt rubber into the asphalt rubber raw materials with a second proportion for processing again when the discharging current is lower than the preset discharging current value, and returning to the step of "shearing the processed asphalt rubber" until the viscosity of the pumped asphalt rubber meets the preset viscosity value, wherein the second proportion is determined according to the discharging current and the preset discharging current value.

The present disclosure further provides a device for controlling viscosity of asphalt rubber based on a current variation. The device comprises an asphalt rubber processing equipment, a shearing machine, a discharging pump and a finished product storage equipment, wherein an output end of the asphalt rubber processing equipment is connected with an input end of the shearing machine; an output end of the shearing machine is connected with an input end of the discharging pump; an output end of the discharging pump is connected with the finished product storage equipment;

wherein, the output end of the shearing machine is further connected with an input end of the asphalt rubber processing equipment; and the output end of the discharging pump is further connected with the input end of the shearing machine and the input end of the asphalt rubber processing equipment.

According to the specific embodiments provided by the present disclosure, the present disclosure has the following technical effects:

According to the method and device for controlling the viscosity of the asphalt rubber based on the current variation provided by the present disclosure, in the shearing stage, whether shearing is completed is determined by obtaining the shearing current, and the viscosity of the asphalt rubber can be preliminarily adjusted in the process of adjusting and controlling the shearing current. Then, in the discharging stage, the discharging current is detected, and meanwhile, the viscosity of the current asphalt rubber can be directly obtained by combining the viscosity-discharging current correlation relationship, so that the problem that manual detection consumes long time can be avoided. Meanwhile, whether the viscosity of the current asphalt rubber is equal to the preset viscosity value, can be determined according to the viscosity of the current asphalt rubber. When the viscosity is not equal to the preset viscosity value, different adjustment and control modes can be selected according to the discharging current, for example, it is possible to select whether to return to the processing stage for continuous processing or to the shearing stage for continuous shearing. The present disclosure adopts double-current control, in which the discharging current is taken as a main part, and the shearing current is taken as an auxiliary part, so that the whole-process control of the processing viscosity of the asphalt rubber is realized, and the accuracy for controlling the viscosity of the asphalt rubber is improved.

In addition, the present disclosure proves that the relationship between the discharging current of the equipment and the asphalt rubber production viscosity can evaluate the viscosity of the asphalt rubber in advance, the viscosity of the asphalt rubber can be adjusted and controlled in time according to needs, and the stability of the asphalt rubber production quality is guaranteed to the maximum extent.

BRIEF DESCRIPTION OF THE DRAWINGS

To more clearly illustrate the embodiment of the present disclosure or the technical solution in the prior art, the accompanying drawings to be used in the embodiment are briefly illustrated. Apparently, the accompanying drawings in the following description show merely some embodiments of the present disclosure, and those skilled in the art may still derive other drawings from these accompanying drawings without creative efforts.

REFERENCE SIGNS

1—asphalt rubber processing equipment; 2—shearing machine; 3—discharging pump; and 4—finished product storage equipment.

DETAILED DESCRIPTION OF THE EMBODIMENTS

The technical solution in the embodiments of the present disclosure is clearly and completely described with reference to the accompanying drawings in the embodiments of the present disclosure. Apparently, the described embodiments are merely a part rather than all of the embodiments of the present disclosure. Based on the embodiments in the present disclosure, all other embodiments obtained by those ordinary in the art without creative labor belong to the scope of the present disclosure.

According to the principle of electrotechnology, when an equipment motor shears a material with large transmission resistance, instantaneous power of the motor is increased with a constant voltage, so that the current of the equipment is increased. Through comparative analysis, a current variation and the viscosity of the processed asphalt rubber have a very remarkable correlation relationship.

The purpose of the present disclosure is to provide a method and device for controlling the viscosity of the asphalt rubber based on the current variation, and the viscosity of the asphalt rubber is timely and accurately adjusted and controlled by detecting a shearing current and a discharging current, so that the asphalt rubber meeting a preset viscosity requirement can be output, accuracy of controlling the viscosity of the asphalt rubber is improved, and stability of asphalt rubber production is ensured.

To make the foregoing objective, features and advantages of the present disclosure clearer and more comprehensible, the present disclosure is further described in detail below with reference to the accompanying drawings and specific embodiments.

Embodiment I

Figure 1:
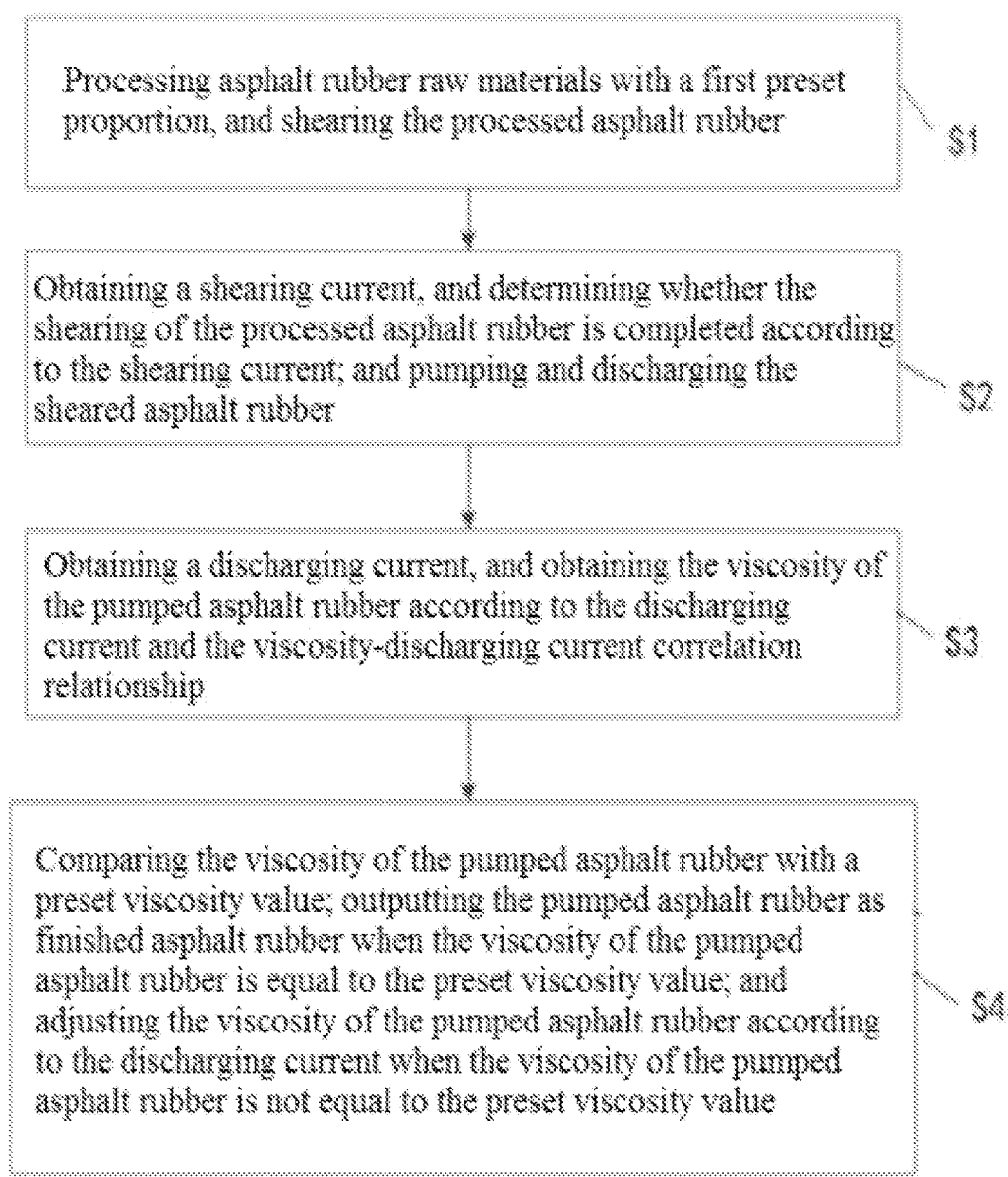
FIG. 1 is a flow chart of a method for controlling the viscosity of the asphalt rubber based on a current variation, according to the first embodiment of the present disclosure.

Referring to FIG. 1, the embodiment provides a method for controlling the viscosity of the asphalt rubber based on current variation, comprising Steps S1-S4:

Step S1: Asphalt rubber raw materials with a first preset proportion is processed, and the processed asphalt rubber is sheared.

For determining when a processing of the asphalt rubber is completed to enter a shearing stage, a processing time is limited in the embodiment, that is, after the processing time reaches a preset processing time, the processing of the asphalt rubber is completed to enter the shearing stage.

Step S2: A shearing current is obtained, it is determined whether shearing of the processed asphalt rubber is completed according to the shearing current, and the sheared asphalt rubber is pumped out.

Step S2 specifically includes:

obtaining the shearing current in a preset shearing time period; and completing the shearing of the processed asphalt rubber when the shearing current is equal to a preset shearing current value;

adding the currently sheared asphalt rubber into the asphalt rubber raw materials with the first proportion for processing again when the shearing current is lower than the preset shearing current value, and returning to the step of "the processed asphalt rubber is sheared" until the shearing current is equal to the preset shearing current value, where the first proportion is determined according to the shearing current and the preset shearing current value; and prolonging the shearing time when the shearing time reaches the preset shearing time and the shearing current is higher than the preset shearing current value, until the shearing current is equal to the preset shearing current value.

In the embodiment, the viscosity of the asphalt rubber can be preliminarily determined by detecting the shearing current. In the preset shearing time period, when the shearing current is lower than the preset shearing current value, it indicates that over shearing or insufficient feeding occurs, so that the viscosity of the sheared asphalt rubber is lower than the set value, and therefore, the sheared asphalt rubber at the moment needs to enter into the processing stage again, and the appropriate asphalt rubber raw materials are added when the processing is carried out again. When the shearing time reaches the preset shearing time and the shearing current is higher than the preset shearing current value, it indicates that the viscosity of the sheared asphalt rubber at the moment is high, the sheared asphalt rubber needs to be sheared continuously, and the viscosity of the asphalt rubber is preliminarily adjusted by delaying the shearing time.

For the setting of the preset shearing current value, the preset shearing current can be set to be a first preset shearing current value of 98 A and a second preset shearing current value of 109 A under the condition that the shearing current value in the general shearing process is 98-109 A. When the shearing current is lower than the preset shearing current value, the shearing current needs to be compared with the first preset shearing current value of 98 A; and when the shearing current is higher than the preset shearing current value, the shearing current needs to be compared with the second preset shearing current value of 109 A.

However, when the shearing current detected in the shearing process is always 98-109 A, a preset shearing current value may also be set in the range of 98-109 A to adjust the viscosity of the asphalt rubber more accurately and preliminary, such as 104 A or 105 A, according to actual needs.

Step S3: A discharging current is obtained, and the viscosity of the pumped asphalt rubber is obtained according to the discharging current and the viscosity-discharging current correlation relationship.

Figure 2:
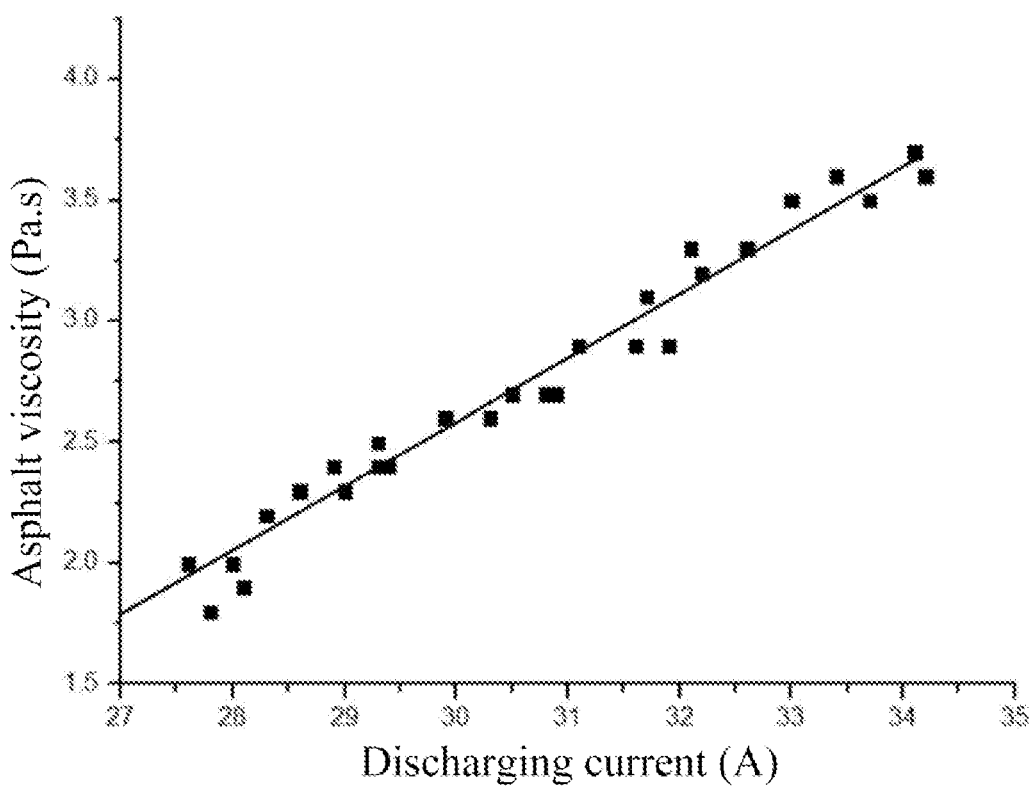
FIG. 2 is a curve diagram of a viscosity-discharging current correlation, according to the first embodiment of the present disclosure.

In the embodiment, the viscosity and the discharging current are of extremely high positive linear correlation, and the viscosity of the asphalt rubber can be better evaluated by the discharging current, so that the viscosity of the asphalt rubber can be deduced by the viscosity-discharging current correlation and the discharging current value, where the viscosity-discharging current correlation is summarized by multiple asphalt rubber processes in the actual production process, and a obtaining process of the viscosity-discharging current correlation comprises the following steps:

processing asphalt rubber raw materials with a second preset proportion, shearing the processed asphalt rubber, and pumping and discharging the sheared asphalt rubber;

obtaining the discharging current, and meanwhile detecting the viscosity of the pumped asphalt rubber;

adjusting the value of the second preset proportion again, and returning to the step of "the asphalt rubber raw materials with a second preset proportion is processed" until multiple groups of the discharging current and viscosity of the pumped asphalt rubber are obtained; and carrying out curve fitting on the multiple groups of the discharging current and the viscosity of the pumped asphalt rubber to obtain the viscosity-discharging current correlation relationship, as shown in FIG. 2.

Where, an expression of the viscosity-discharging current correlation relationship is that $y=0.26x-5.32$, where y represents the viscosity of the pumped asphalt rubber, x represents the discharging current, and the Pearson's correlation coefficient r is equal to 0.98326.

In addition, the discharging current can be intuitively obtained in the discharging stage, and the current viscosity value of the asphalt rubber can be directly obtained by combining the viscosity-discharging current correlation relationship under the condition that the viscosity of the asphalt rubber does not need to be manually detected, so that the problem of long manual detection time due to actual measurement of a laboratory rotary viscometer according to a standard method can be avoided, and the viscosity detection efficiency is improved.

Step S4: The viscosity of the pumped asphalt rubber is compared with a preset viscosity value;

when the viscosity of the pumped asphalt rubber is equal to the preset viscosity value, the pumped asphalt rubber is output as finished asphalt rubber; and when the viscosity of the pumped asphalt rubber is not equal to the preset viscosity value, the viscosity of the pumped asphalt rubber is adjusted according to the discharging current. The process specifically includes the following steps:

shearing the pumped asphalt rubber again when the discharging current is higher than a preset discharging current value, and returning to the step of "the shearing current is obtained" until the viscosity of the pumped asphalt rubber meets the preset viscosity value; and adding the pumped asphalt rubber into the asphalt rubber raw materials with a second proportion for processing again when the discharging current is lower than the preset discharging current value, and returning to the step of "the processed asphalt rubber is sheared", until the viscosity of the pumped asphalt rubber meets the preset viscosity value, where the second proportion is determined according to the discharging current and the preset discharging current value.

In order for those skilled in the art to more clearly understand the double-current control in the present solution, several solutions are now provided for illustration:

In the first solution, feeding is carried out according to a normal formula. When the materials pass through the shearing machine, the shearing current is 100 A and is close to the lower limit within 98 A-109 A (which can be understood as being lower than the preset value of 104 A). The shearing time is not prolonged, and the appropriate raw materials are added for processing again in the processing stage. After shearing, the discharging current is about 29 A, the calculated viscosity is 2.2 Pa·s, and the laboratory detection viscosity is 2.1 Pa·s. The workability of the construction is good, and the materials can be directly discharged. Where, the laboratory detection viscosity is used for further rechecking the viscosity of the processed asphalt rubber and ensuring that the viscosity of the asphalt rubber is stable and appropriate.

In the second solution, feeding is carried out according to a normal formula. When the materials pass through the shearing machine, the shearing current is 106 A and is close to the upper limit within 98 A-109 A (which can be understood as being higher than the preset value of 104 A). The shearing time is appropriately prolonged, and after shearing, the discharging current is about 30 A, the calculated viscosity is 2.5 Pa·s, and the laboratory detection viscosity is 2.6 Pa·s. The workability of the construction is good, and the materials can be directly discharged.

In the third solution, feeding is carried out according to a normal formula. When the materials pass through the shearing machine, the shearing current is 98 A and is close to the lower limit within 98 A-109 A. The shearing time is not prolonged, and after shearing, the discharging current is about 27 A, the calculated viscosity is 1.7 Pa·s, and the laboratory detection viscosity is 1.6 Pa·s, which is slightly lower. The feeding ratio is appropriately adjusted, and the materials are pumped back to a processing tank for continuous processing.

In the fourth solution, feeding is carried out according to a normal formula. When the materials pass through the shearing machine, the shearing current is 108 A and is close to the upper limit within 98 A-109 A. The shearing time is appropriately prolonged, and after shearing, the discharging current is about 33 A, the calculated viscosity is 3.3 Pa·s, and the laboratory detection viscosity is 3.3 Pa·s, which is slightly higher. The materials are appropriately pumped back for continuous shearing.

In the embodiment, a double-current control is adopted, the discharging current is taken as a main part, and the shearing current is taken as an auxiliary part, so that the whole-process control of processing viscosity of the asphalt rubber can be realized, and the accuracy for controlling the viscosity of the asphalt rubber viscosity is improved. The control process is ingenious in design, the control of the viscosity is simple and accurate, continuous and stable production of the asphalt rubber can be achieved, and the production efficiency is high.

Embodiment II

Figure 3:
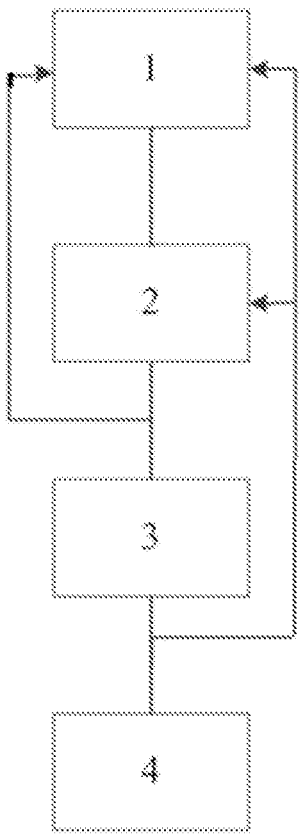
FIG. 3 is a structure diagram of a device for controlling viscosity of asphalt rubber based on current variation, according to the second first embodiment of the present disclosure.

Referring to FIG. 3, the embodiment provides a device for controlling viscosity of asphalt rubber based on a current variation, comprising:
an asphalt rubber processing equipment 1, a shearing machine 2, a discharging pump 3 and a finished product storage equipment 4, where an output end of the asphalt rubber processing equipment 1 is connected with an input end of the shearing machine 2; an output end of the shearing machine 2 is connected with an input end of the discharging pump 3; an output end of the discharging pump 3 is connected with the finished product storage equipment 4.

The output end of the shearing machine 2 is further connected with an input end of the asphalt rubber processing equipment 1; and the output end of the discharging pump 3 is further respectively connected with the input end of the shearing machine 2 and the input end of the asphalt rubber processing equipment 1.

In the embodiment, the device only relates to the four structures of the asphalt rubber processing equipment, the shearing machine, the discharging pump and the finished product storage equipment. The structure of the device is simple, and more accurate control of the viscosity of the asphalt rubber can be completed based on the simple structure.

Several examples are used for illustration of the principles and implementation methods of the present disclosure. The description of the embodiments is used to help illustrate the method and the core principles of the present disclosure; and meanwhile, those skilled in the art can make various modifications in terms of specific embodiments and scope of application in accordance with the teachings of the present disclosure. In conclusion, the content of this specification shall not be construed as a limitation to the present disclosure.

What is claimed is:

1. A method for controlling viscosity of asphalt rubber based on a current variation, comprising:
    processing asphalt rubber raw materials with a first preset proportion, and shearing the processed asphalt rubber;
    obtaining a shearing current, and determining whether the shearing of the processed asphalt rubber is completed according to the shearing current; and pumping and discharging the sheared asphalt rubber;
    obtaining a discharging current, and obtaining the viscosity of the pumped asphalt rubber according to the discharging current and the viscosity-discharging current correlation relationship;
    comparing the viscosity of the pumped asphalt rubber with a preset viscosity value; and outputting the pumped asphalt rubber as finished asphalt rubber when the viscosity of the pumped asphalt rubber is equal to the preset viscosity value; and
    adjusting the viscosity of the pumped asphalt rubber according to the discharging current when the viscosity of the pumped asphalt rubber is not equal to the preset viscosity value.

2. The method according to claim 1, wherein before the processed asphalt rubber is sheared, a processing time is required to reach a preset processing time.

3. The method according to claim 1, wherein obtaining the shearing current and determining whether the shearing of the processed asphalt rubber is completed according to the shearing current comprises:
    obtaining the shearing current in a preset shearing time period; and completing the shearing of the processed asphalt rubber when the shearing current is equal to a preset shearing current value;
    adding the currently sheared asphalt rubber into the asphalt rubber raw materials with a first proportion for processing again when the shearing current is lower than the preset shearing current value, and returning to the step of shearing the processed asphalt rubber until the shearing current is equal to the preset shearing current value, wherein the first proportion is determined according to the shearing current and the preset shearing current value; and
    prolonging the shearing time when the shearing time reaches the preset shearing time and the shearing current is higher than the preset shearing current value, until the shearing current is equal to the preset shearing current value.

4. The method according to claim 1, wherein obtaining the viscosity-discharging current correlation relationship comprises:
- processing asphalt rubber raw materials with a second preset proportion, shearing the processed asphalt rubber, and pumping and discharging the sheared asphalt rubber;
- obtaining the discharging current, and meanwhile detecting the viscosity of the pumped asphalt rubber;
- adjusting the value of the second preset proportion again, and returning to the step of processing asphalt rubber raw materials with a second preset proportion until multiple groups of the discharging current and viscosity of the pumped asphalt rubber are obtained; and
- carrying out curve fitting on the multiple groups of the discharging current and viscosity of the pumped asphalt rubber to obtain the viscosity-discharging current correlation relationship.

5. The method according to claim 4, wherein an expression of the viscosity-discharging current correlation relationship is $y=0.26x-5.32$, wherein y represents the viscosity of the pumped asphalt rubber, and x represents the discharging current.

6. The method according to claim 1, wherein adjusting the viscosity of the pumped asphalt rubber according to the discharging current when the viscosity of the pumped asphalt rubber is not equal to the preset viscosity value comprises:
- shearing the pumped asphalt rubber again when the discharging current is higher than a preset discharging current value, and returning to the step of obtaining the shearing current until the viscosity of the pumped asphalt rubber meets the preset viscosity value; and
- adding the pumped asphalt rubber into the asphalt rubber raw materials with a second proportion for processing again when the discharging current is lower than the preset discharging current value, and returning to the step of shearing the processed asphalt rubber until the viscosity of the pumped asphalt rubber meets the preset viscosity value, wherein the second proportion is determined according to the discharging current and the preset discharging current value.

* * * * *